US006803224B2

(12) United States Patent
Ramirez et al.

(10) Patent No.: US 6,803,224 B2
(45) Date of Patent: Oct. 12, 2004

(54) REGULATED EXPRESSION OF CLONED GENES USING A CASCADE GENETIC CIRCUIT

(75) Inventors: Angel Cebolla Ramirez, Sevilla (ES); Carolina Sousa Martin, Sevilla (ES); Victor de Lorenzo Prieto, Sevilla (ES)

(73) Assignee: Counsejo Supeslor de Investigaciones Cientificas, Madrid (ES)

( * ) Notice: Subject to any disclaimer, the term of this patent is extended or adjusted under 35 U.S.C. 154(b) by 103 days.

(21) Appl. No.: 09/746,567

(22) Filed: Dec. 21, 2000

(65) Prior Publication Data

US 2001/0016354 A1 Aug. 23, 2001

Related U.S. Application Data

(63) Continuation of application No. PCT/IB00/00830, filed on Jun. 22, 2000.

(51) Int. Cl.[7] .......................... C12N 1/21; C12N 15/63; C07H 21/04
(52) U.S. Cl. ............... 435/252.33; 435/455; 435/252.3; 435/252.34; 435/320.1; 536/23.1; 536/23.2; 536/24.1; 536/24.2
(58) Field of Search .................... 435/252.3, 252.33, 435/455, 252.34, 320.1; 536/23.1, 23.2, 24.1, 24.2

(56) References Cited

FOREIGN PATENT DOCUMENTS

| EP | 0 455 424 A2 | 11/1991 |
|----|---|---|
| WO | WO 90/08830 | 8/1990 |
| WO | WO 98/08958 | 3/1998 |
| WO | WO 00/78976 | 12/2000 |

OTHER PUBLICATIONS

Aubrecht et al. Controlled gene expression in mammalian cells via a regulatory cascade involving the tetracycline transactivator and lac repressor. Gene. Jun. 26, 1996; 172(2):227–31.*
Dubendorff et al., Controlling Basal Expression in an Inducible T7 Expression System by Blocking the Target T7 Promoter with *lac* Repressor, *J. Mol. Biol* 219: 45–59 (1991).
Ramos et al., Signal–Regulator Interactions. Genetic Analysis of the Effector Binding Site of xylS, the Benzoate–activated Positive Regulator of *Pseudomonas* TOL Plasmid Meta–Cleavage Pathway Operon, *J. Mol. Biol.* 211:373–382 (1990).
Bentley et al., Biotechnology and Bioengineering, 35:668–681 (1990).
Cebolla and Palomares, Microbiologia SEM, 10:371–384 (1994).
Cebolla et al., Appl. Environ. Microbiol., 59:2511–2519 (1993).
Cebolla et al., J. Biol. Chem., 272:3986–3992 (1997).
Cebolla et al., Nuc. Acids. Res., 29:3:759–766 (2001).
de Lorenzo, Trends Biotechnol., 12:365–371 (1994).
de Lorenzo and Timmis, Methods in Enzymology, 235:386–405 (1994).
de Lorenzo et al., Gene, 130:41–46 (1993).
Dong et al, J. Bacteriol., 177:1497–1504 (1995).
Egan and Schleif, J. Mol. Biol., 234:87–98 (1993).
Fellay et al., Gene, 52:147–154 (1987).
Fernandez et al., Mol. Microbiol., 16:205–213 (1995).
Figge et al., Cell, 52:713–722 (1988).
Gallegos et al., Nuc. Acids Res., 21:807–810 (1993).
Gutierrez and Devedjian, Nuc. Acids Res., 17:3999 (1989).
Herrero et al., J. Bacteriol., 172:6557–6567 (1990).
Huang and Schell., The J. of Biol. Chem., 266:10830–10838 (1991).
Inouye et al., J. Bacteriol., 169:3587–3592 (1987).
Inouye et al., Proc. Natl. Acad. Sci. USA, 84:5182–5186 (1987).
Kahn et al., Methods in Enzymology, 68:268–280 (1979).
Kessler et al., J. Bacteriol., 176:3171–3176 (1994).
Laemmli, Nature, 227:680–685 (1970).
Makrides, Microbiol. Reviews, 60:512–538 (1996).
Mertens et al., Bio/Technology, 13:175–179 (1995).
Nilsson and Skogman, Bio/Technology, 4:901–903 (1986).
Ramos et al., Annu. Rev. Rev. Microbiol., 51:341–373 (1997).
Ramos et al., Nuc. Acids Res., 18:2149–2152 (1990).
Ramos et al., Proc. Natl. Acad. Sci. USA, 83:8467–8471 (1986).
Schein, Bio/Technology, 7:1141–1149 (1989).
Sousa et al., Microbiology, 143:2071–2078 (1997).
Suarez et al., Appl. Environ. Microbiol., 63:122–127 (1997).
Vilette et al., Mol. Microbiol., 17:493–504 (1995).
Yanisch–Perron et al., 33:103–119 (1985).

* cited by examiner

*Primary Examiner*—David Guzo
*Assistant Examiner*—Daniel M Sullivan
(74) *Attorney, Agent, or Firm*—Bio Technology Law Group; Daniel M. Chambers; Edward O. Kreusser (57) ABSTRACT

The present invention relates to the design, preparation and use of cascade regulatory circuits for amplification of gene expression. The genetic circuit is based on a plurality (e.g., two or more) of regulatory genes organized in a hierarchical order of expression in a genetic construct or constructs, which can be established in a cell, e.g., a gram-negative bacteria, by means of autoreplicative vectors or by chromosomal insertion. In one embodiment, the genetic construct(s) can be stabily maintained in the chromosome without selective pressure, and gene expression induced three orders of magnitude therefrom using economical biodegradable benzoate derivatives.

33 Claims, 4 Drawing Sheets

SEQUENCE LISTING

<160> NUMBER OF SEQ ID NOS: 6

<210> SEQ ID NO 1
<211> LENGTH: 23
<212> TYPE: DNA
<213> ORGANISM: Escherichia coli

<400> SEQUENCE: 1
gcaaatttcc aggcatcaaa taa                    23

```
<210> SEQ ID NO 2
<211> LENGTH: 23
<212> TYPE: DNA
<213> ORGANISM: Escherichia coli

<400> SEQUENCE: 2
gggaattccc tggcagttta tgg                                           23

<210> SEQ ID NO 3
<211> LENGTH: 26
<212> TYPE: DNA
<213> ORGANISM: Escherichia coli

<400> SEQUENCE: 3
gtgtcaaatt tgatagggat aagtcc                                        26

<210> SEQ ID NO 4
<211> LENGTH: 27
<212> TYPE: DNA
<213> ORGANISM: Escherichia coli

<400> SEQUENCE: 4
gcctgaattc aggcattgac gaaggca                                       27

<210> SEQ ID NO 5
<211> LENGTH: 28
<212> TYPE: DNA
<213> ORGANISM: Escherichia coli

<400> SEQUENCE: 5
gaggaattca atctagaggg tattaata                                      28

<210> SEQ ID NO 6
<211> LENGTH: 28
<212> TYPE: DNA
<213> ORGANISM: Escherichia coli

<400> SEQUENCE: 6
cgggatcccc gttgtccgga cgagtgcc                                      28
```

REGULATED EXPRESSION OF CLONED GENES USING A CASCADE GENETIC CIRCUIT

RELATED APPLICATIONS

This application is a continuation of and claims priority to PCT Application PCT/IB00/00830, filed Jun. 22, 2000, in the name of Ramirez, et al., entitled "Regulated expression of cloned genes using a cascade genetic circuit;" and additionally claims priority to Spanish Application ES-200001389, filed May 31, 2000, in the name of Ramirez, et al., entitled "Regulated expression of cloned genes using a cascade genetic circuit," and to Spanish Patent Application ES-9901383, filed Jun. 22, 1999, in the name of Ramirez, et al., entitled "Tightly regulated overexpression of cloned genes using a cascade genetic circuit," each of which applications is herein incorporated by reference in its entirety, including all drawings.

FIELD OF THE INVENTION

The present invention relates to the design of transcriptional cascade circuits to amplify gene expression. It also relates to the use of these systems for the overproduction of polypeptides such as therapeutic proteins, enzymes, hormones, growth factors, and apoliproteins in vitro, and in cells, i.e., cell cultures. This has great industrial utility, e.g., in the biotechnology and pharmaceutical industries.

BACKGROUND OF THE INVENTION

Overexpression of cloned genes is very convenient for production of either recombinant polypeptides or specific cell metabolites for basic research, and the pharmaceutical and biotechnology industries generally. Production of large amounts of cloned genes has traditionally been achieved by combining gene amplification with strong promoters regulated by repressors. However, these conventional strategies typically have the disadvantages that: 1) maintenance of plasmid expression vectors typically requires selection with antibiotics, giving rise to metabolic burden and additional costs for large scale industrial production (Nilson and Skogman 1986); 2) low level expression is indicated when dealing with toxic proteins, and in avoiding accumulation of mutations in the recombinant protein products themselves (Mertens et al., 1995; Vilette et al. 1995), which is difficult to achieve when the cloned gene is in multicopy due to the multiple copy number of traditional plasmid vectors and the high basal ("leaky") level of expression of most traditionally used promoters, e.g., tac or trc; 3) traditional inducers, e.g., IPTG in lac expression systems, are expensive and have a certain degree of toxicity (Figge et al. 1988); 4) high expression of recombinant proteins has been shown to reduce host cell growth rate and, concomitantly, overall protein synthesis (Bentley et al., 1990; Dong et al. 1995), presumably due to increased metabolic burden on the host; and 5) a considerable number of existing expression systems only replicate in E. coli, which may limit expression of certain proteins, e.g., those desired to be secreted.

An alternative expression system that fulfills some of the above requirements uses miniTn5 transposon vectors (de Lorenzo and Timmis 1994) to insert heterologous genes into the bacterial chromosome, thereby allowing high stability of expression (Cebolla et al. 1993; Suarez et al. 1997). Suarez in particular describes the stable production of pertusic toxin in *Bortedetella bronchiseptica* by miniTn5-mediated chromosomal insertion and expression using a salicylate regulatory system. Salicylate is a benzoate inducer 1000-fold less expensive than IPTG (SIGMA catalog 1998). The system is based on the nahR regulatory gene, which encodes a positive regulator activated by salicylate and its target promoter Psal (de Lorenzo et al. 1993). However, expression levels obtained are relatively poor (0.1% of total proteins). This low level is likely because the genes are in monocopy in the chromosome.

If yield could be improved while maintaining the advantages of low basal levels, stability, broad host range, and low cost, the nahR/Psal regulatory system would have great industrial utility.

SUMMARY OF THE INVENTION

We have designed a cascade system that allows 10 to 20 fold greater expression over the standard nahR/Psal system while substantially retaining one or more of that system's innate advantages. To achieve this, another regulatory element, xylS2 and its target promoter Pm, is coupled to Psal expression in a cascade circuit. The xylS2 regulatory gene responds to the common inducer and has more gene expression capacity than standard nahR/Psal. Synergistic activation of the Pm promoter by the XylS2 transcriptional activator can be achieved by simultaneously increasing the intracellular concentration and specific activity of activator/regulator in the presence of a common benzoate derivative inducer, e.g., salicylate.

Accordingly, in a first aspect the invention features a cascade genetic circuit comprising one or more nucleic acid constructs encoding a plurality of transcriptional regulators, said encoded regulators arranged in a hierarchical order such that expression of an upstream regulator from said plurality stimulates expression of a downstream regulator from said plurality; and a final target promoter, said final target promoter responsive in a dose-dependent fashion to a terminal downstream regulator of said plurality of regulators.

In certain preferred embodiments, it may be useful to introduce the final target promoter alone, e.g., via PCR, into a host genome at designated position to determine effect on expression of the downstream sequence. To do this, it may first be desirable to disable or knock out the native promoter, gene, or nucleic acid sequence. In other preferred embodiments, as described below, heterologous genes and sequences are preferred for use with the cascade circuit and, accordingly, may be introduced.

In one especially preferred embodiment, the cascade genetic circuit further comprises a multiple cloning site downstream of the final target promoter.

In another preferred embodiment, the cascade genetic circuit, or at least a portion thereof, is present as a chromosomal integration in a host cell. In a different, not necessarily mutually exclusive embodiment, at least one of said one or more nucleic acid constructs is present as an autoreplicative plasmid.

In a further embodiment, the cascade genetic circuit, or at least a portion thereof, is responsive to an inducer, preferably an inducer that is capable of inducing the expression of more than one regulator in the cascade. In preferred embodiments, the inducer is a benzoate derivative, preferably, although not necessarily, salicylate.

In another aspect, the invention features a cell, tissue, or organism comprising the cascade genetic circuit of any of the preceding claims. Preferably, the cell is selected from the group consisting of procaryotic and eukaryotic cells. As concerns eukaryotic cells, mammalian, insect, yeast, and plant cells are preferred. As concerns procaryotic cells, gram-negative bacterial cells are preferred.

In yet another aspect, the inventon features methods of regulating the expression of a nucleic acid sequence, comprising establishing a cascade genetic circuit according to any of the cascade genetic circuit embodiments described above; placing said nucleic acid sequence under control of said final target promoter; and inducing said cascade genetic circuit to stimulate expression of said nucleic acid sequence.

Preferably the nucleic acid sequence encodes a polypeptide selected from the group consisting of enzymes, hormones, growth factors, apolipoproteins, therapeutic proteins, diagnostic proteins, and portions or derivatives thereof. In other preferred embodiments, the nucleic acid sequence encodes an anti-sense molecule, ribozyme, rRNA, tRNA, snRNA, or simply a diagnostic RNA molecule. In certain preferred embodiments, the nucleic acid encodes a reporter gene product useful in diagnostics.

DETAILED DESCRIPTION OF THE INVENTION

By using regulatory genes of the control circuits for the expression of catabolic operons, a cascade expression system for amplifying gene expression was constructed. The system is based on the activation characteristics of the Pm promoter by the XylS2 mutant transcriptional activator. Strength of Pm activation depends on both the amount of XylS2 protein and its specific activity, which is enhanced by the presence of salicylate and other benzoate derivatives. To couple the increase of XylS2 intrinsic activity and XylS2 intracellular concentration, the expression of xylS2 is under the control of the Psal promoter and the NahR transcriptional activator, that is also activated in response to common inducers. The synergistic action of both transcriptional regulators lead to 10 to 20-fold amplification of the gene expression capacity with regard to each individual expression system.

One embodiment of the system comprises a cassette having the regulatory genes nahR/Psal::xylS2 flanked by transposable sequences which facilitate stable insertion into the chromosome of a cell, e.g., a gram negative bacteria. A complementary expression module containing the target promoter Pm upstream of a multicloning site for facilitating the cloning of a recombinant DNA is used as part of the system. The expression module can be introduced in multicopy plasmid form or else transferred to the chromosome, e.g., via minitransposon delivery vectors (if either stability of the expression and/or the lowest basal level are desired). To achieve this, the expression module with the Pm promoter and the heterologous gene/s are preferably flanked by rare restriction sites, e.g., NotI, for further cloning utility.

An ideal expression system should be tighly regulated (i.e. to have very low basal level of expression and a high level of expression in the presence of inducer). For large scale fermentations, it is very convenient that the inducer be cheap and that the overexpression of the gene be stable, preferably without selective pressure. The capacity of the culture to reach high biomass should be affected as little as possible, and convenient for use in a broad range of organisms. Salicylate-induced expression using nahR/Psal in the chromosome of gram negative bacteria has proven to be very stable and tightly regulated (Suarez et al. 1996). However, the expression level obtained is very low due to single copy presence and limited gene expression capacity.

In contrast, the xylS/Pm expression system has shown to have an outstanding range of activity that depends both on the specific activity of the XylS transcriptional regulator and on the intercellular concentration of XylS; manipulation of either affects expression (Kessler et al. 1994).

The transcriptional activity of Pm in vivo appears to be non-saturable because, despite overexpression of XylS, expression from Pm continues in response to 3-methylbenzoate inducer. However, the expression systems based on the xylS/Pm system maintain constant amounts of xylS expression, which waste the potential increment in gene expression capacity if xylS expression could be made inducible. As the Applicants demonstrate herein, this can be achieved by coupling the expression of xylS to another expression system (first system). If the signal that induces transcriptional regulator expression were the same that the one that activates it, the signal could produce synergy in the activation of gene expression from the Pm promoter.

Figure 2A:
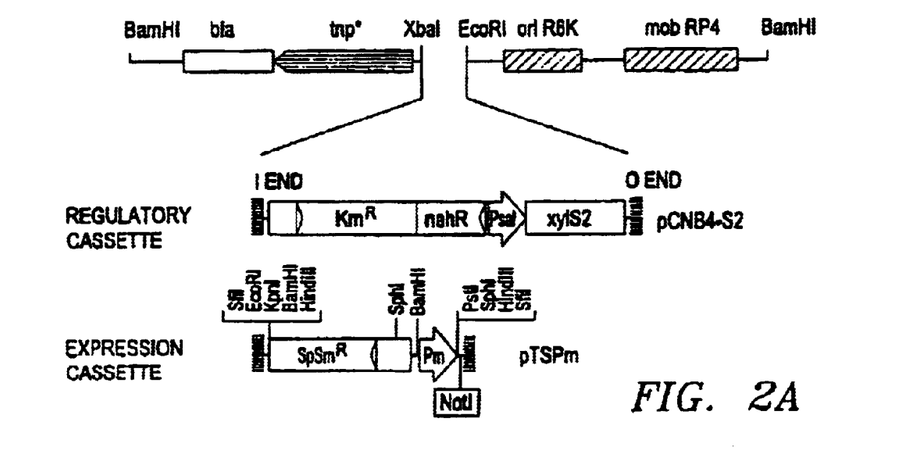

The present invention describes this: synergistic signal amplification using coupled expression systems. To use regulators responding to a common signal, nahR/Psal was used as a first regulatory system and xylS2, a mutant of xylS able to respond to salicylate (Ramos et al. 1986), as a second regulatory system. A 1.2 Kb fragment with the xylS2 gene was cloned by digestion with HindIII and partial digestion with NcoI, and insertion in the same sites of pFH2 (Table 1). The resultant plasmid pNS2 was digested with NotI and the fragment with xylS2 was inserted into the plasmid pCNB4 (de Lorenzo et al. 1993). This regulator is left under the control of the nahR/Psal system and flanked by the insertion sequences of miniTn5. The resultant plasmid pCNB4-S2 (FIG. 2a) has a R6K replication origin (Kahn et al. 1979), that can only replicate in strains expressing π protein. E. coli λpir lysogen can express that protein and thus, replicate the miniTn5 delivery plasmid (Herrero et al. 1990).

Figure 1:
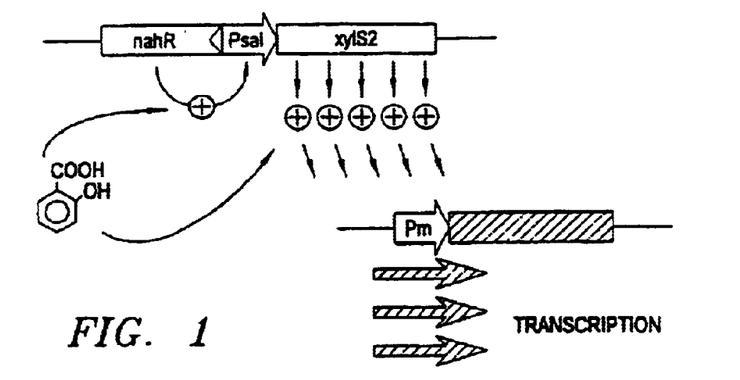
FIG. 1. Schematic representation of a cascade regulatory circuit embodiment. An expression cassette containing the nahR gene and the Psal promoter controls the expression of xylS2. In the presence of a common inducer, NahR activates the expression of xylS2. Simultaneous high intracellular levels of XylS2 and stimulation of XylS2 specific transcriptional activity achieves amplified expression levels of a given gene under control of the Pm promoter.

By using the donor strain of miniTn5 vectors S17-1(λpir) one can transfer the regulatory cassette to other gram negative strains using standard biparental conjugation, and select for recipient bacteria using selective markers determined from the minitransposon (Herrero et al. 1990; de Lorenzo and Timmis 1994). To verify that it is an insertion by transposition and that the plasmid R6K has not been inserted, the transconjugant colonies are checked for the loss of β-lactamase of the suicide plasmid. Every strain with the regulatory cassette nahR/Psal::xylS2 would produce the regulatory protein XylS2 in response to salicylate (FIG. 1).

This strain can then be used for insertion by conjugation or transformation of a second regulatory cassette that contains the Pm promoter fused to the heterologous gene of interest. One such construct, pTSPm, is a miniTn5 vector that contains within the insertion sequences a streptomycin resistance gene, the Pm promoter, and a NotI restriction site (FIG. 2a) to insert the heterologous gene.

To construct pTSPm, a fragment with the omega interposon (Fellay et al. 1987) was inserted in the BamHI site of the vector pUC18Sfi-Km$^R$-xylS-Pm-Sfi (de Lorenzo et al. 1993) which removed a fragment with Km$^R$ and xylS. The resultant plasmid was digested with SfiI and the biggest fragment was cloned into the pUT backbone of a miniTn5 vector (Herrero et al. 1990) to obtain the plasmid pTSPm. Auxiliary vectors of Table 1 can be used to clone the heterologous genes and then subclone into the NotI site of pTSPm.

Figure 2B:
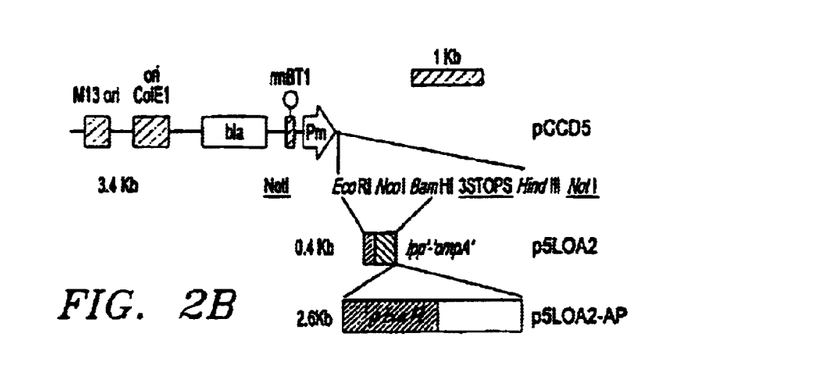
Figure 3:
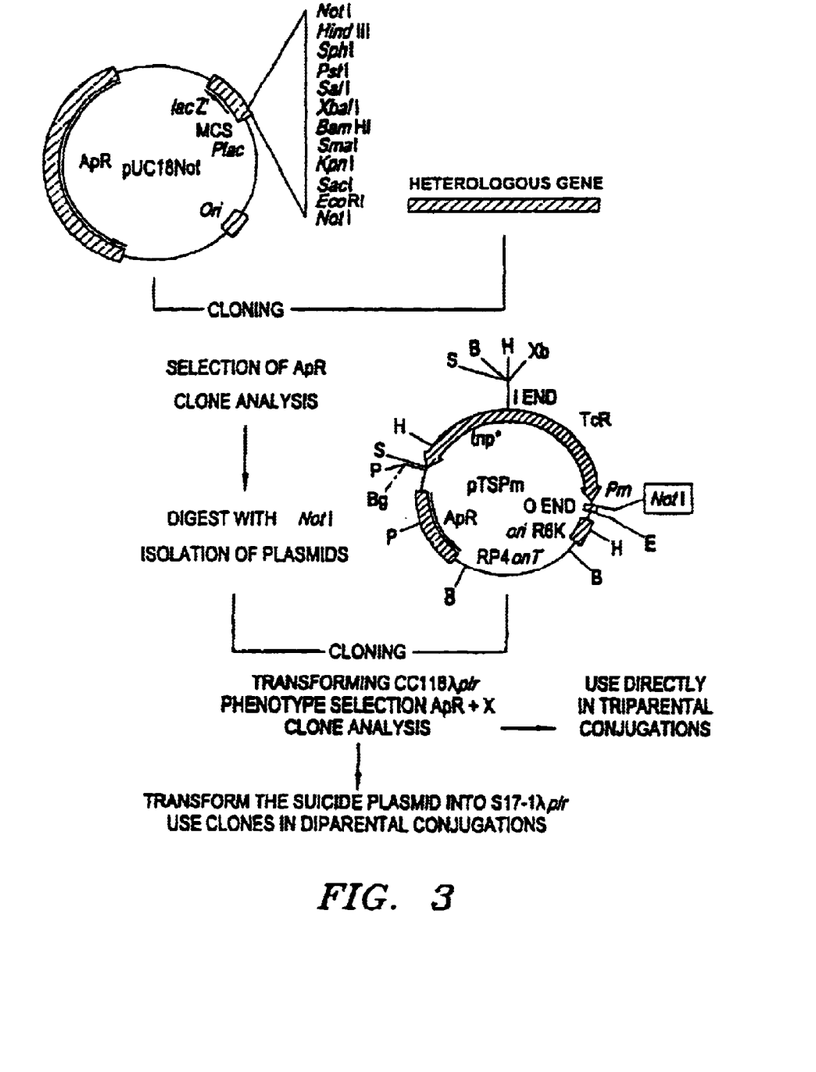
FIG. 3. Embodiment scheme of an example of the construction of miniTn5 vectors for an insertion in monocopy of the heterologous genes by transposition. tnp* is the transposase gene. The insertion sequences are named I end and O end which are substrate of the transposase. DNA flanked by the insertion sequences can be transposed to the receptor strain. The NotI site serves to introduce within the insertion sequences any gene that has been previously cloned in the auxiliary vectors that contain multiple cloning sites flanked by NotI sites (Table 1 and for instance, pUC18Not in the scheme)

A second expression vector with a ColE1 replication origen (pCCD5) contains the Pm promoter upstream of a multicloning site, and a good translation initiation sequence for convenience in cloning heterologous genes (FIG. 2b). Plasmid pCCD5 was constructed cloning an ApoI fragment containing the rrnBT1 transcriptional terminator produced as a PCR fragment from pKK232–8 with the oligos 5'-GCAAATTTCCAGGCATCAAATAA-3' (SEQ ID NO: 1) and 5'-GGGAATTCCCTGGCAGTTTATGG-3' (SEQ ID NO: 2), into the EcoRI site of pFH2 (Table 1). Following ligation, a unique EcoRI site results and those plasmids with intact MCSs can be selected. The Pm promoter was obtained by PCR, using the oligos A-Pm (5'-GTGTCAAATTTGATAGGGATAAGTCC-3' (SEQ ID NO:

3)) and Pm-E (5'-GCCTGAATTCAGGCATTGACGAAGGCA-3' (SEQ ID NO: 4)) as primers, and pUC18Sfi-Km$^R$-xylS-Pm-Sfi as template. Digestion with ApoI (underlined) of the amplified fragment (0.4 Kb) gave a fragment compatible with EcoRI termini, but only the extreme of the fragment downstream of the Pm promoter regenerated the EcoRI site in the junction. Therefore, introduction of the Pm ApoI fragment in the proper sense into the EcoRI linearized intermediate plasmids, rendered vectors that contained the Pm promoter preceeding an intact MCS, with all the key elements flanked by NotI sites.

This last feature may allow to clone in mini-Tn5 delivery vectors if monocopy or stability of the expression system are required. There exists up to 8 different makers in miniTn5 vectors with the NotI site where the Pm fusion may be cloned (de Lorenzo 1994). The resultant vectors may then be inserted into the chromosome of the receptor bacteria by conjugation. Alternatively, cloned genes in pCCD5 under Pm control may be transformed in strains with the regulatory cassette in the chromosome to overexpress the heterologous gene from the plasmid.

BRIEF DESCRIPTION OF THE DRAWINGS

FIG. 2. Vector scheme embodiments for expression of a genetic circuit embodiment. (a) Constructed miniTn5 vectors. The scheme in the upper part represents the backbone of the suicide plasmid pUT with the replication origen R6K (oriR6K), the transposase gene (tnp*), the β-lactamase gene that confers ampicilin resistance (bla), the mobilization origen (mob), and the insertion sequences (I end and O end) represented as horizontal hatched lines. The regulatory cassette in pCNB4-S2 and the expression cassette in pTSPm are down the pUT scheme. The restriction site NotI is rare because it recognizes 8 nucleotides. (b) Scheme of the expression vector pCCD5 (linearized) that contains the Pm promoter upstream of a MCS where the heterologous gene can be cloned. It also contains a M13 replication origen that allows to form single stranded DNA plasmids for site directed mutagenesis. As an example, the cloning strategy of the different fragments that form the lpp'-'ompA'-'phoA fussion is shown.

FIG. 4. Comparison of the production of β-galactosidase in Miller Units (MU) between the regulatory cascade system and the simple systems. (a) Kinetic of β-galactosidase production upon addition of inducer. Salicylate 2 mM was added to the cultures (OD600=0.2), and β-galactosidase activity was monitored at different intervals. Empty symbols: without salicylate. Filled symbols: with salicylate 2 mM; nahR/Psal::trp'::'lacZ (square), xylS2/Pm:trp'::'lacZ (triangle), and nahR/Psal::xylS2/Pm::trp'::'lacZ (circle). (b) Production of β-galactosidase at different salicylate concentrations with nahR/Psal (filled circle), xylS2/Pm (triangle) and nahR/Psal::xylS2/Pm (empty circle).

EXAMPLES

Example 1

Comparison of the Overexpression of lacZ in a Cascade Circuit Relative to a Simple Circuit Example 1.1
Construction of a Cascade Circuit This example illustrates the rational basis, construction and validation of a cascade circuit for gene expression relative to a simple circuit.

To test the efficiency of the amplifier genetic circuits, a plasmid that contains a fusion of Pm to trp'::'lacZ was constructed. A NotI fragment with this fusion was cloned into the NotI site of pTSPm, resulting in plasmid pTSPm-lacZ. The Pm fusion was inserted into the chromosome of *E. coli* CC118 (Herrero 1990) by mating with the donor strain S17-1(λpir) that contained the plasmid pTSPm-lacZ in LB-citrate 0.8% at 30° C. for 4 hours. The pool of bacteria growing on streptomycin 25 mg/l and rifampicin 50 mg/l was used as recipient in a mating with donor strain *E. coli* S17-1(λpir) (pCNB4-S2). To select transconjugants, the mating product was plated onto LB plates with rifampicin, streptomycin and kanamycin (25 mg/l). Ten colonies sensitive to ampicillin (100 mg/l) were selected for further analysis of β-galactosidase activity (Miller 1972). Cultures from colonies of the transconjugant were grown overnight in LB medium (yeast extract 5 g/l, tryptone 10 g/l, 5 g/l NaCl) at 37° C. by shaking. Cultures were diluted 1:100 in fresh media without antibiotic selection and incubated for 2 hours at 37° C. Salicylate (2 mM) was added to the cellular suspensions, which were then shaken at 30° C. for 5 hours. Production of β-galactosidase without inducer ranged between 100 and 400 Miller Units depending on the transconjugant. The lacZ expression could be dramatically induced when the cultures were induced with salicylate up to 25,000–50,000 MU, which corresponded to a gene expression capacity of 150 to 400 times depending on the transconjugant. Variation in the expression level and capacity among the transconjugants is likely due to the proximity to the origen of replication OriC because there are more average gene copies per cell (Sousa et al. 1997).

Figure 4A:
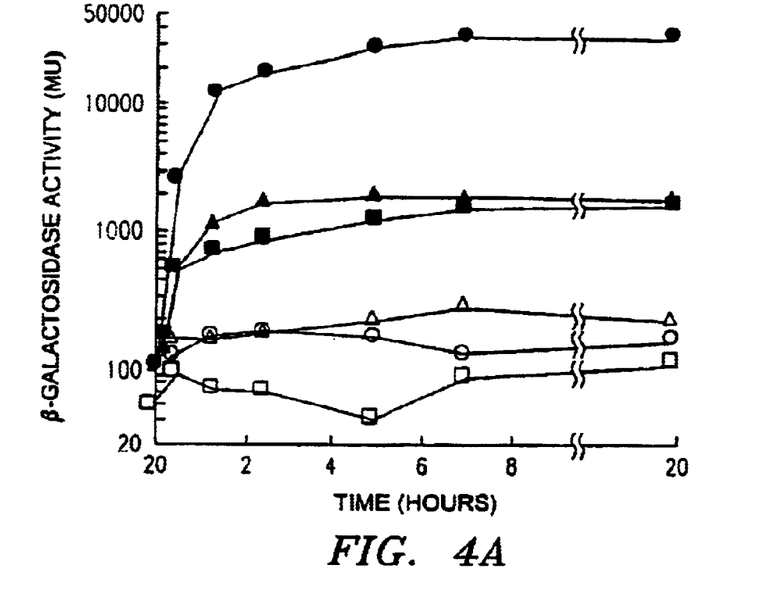
Figure 4B:
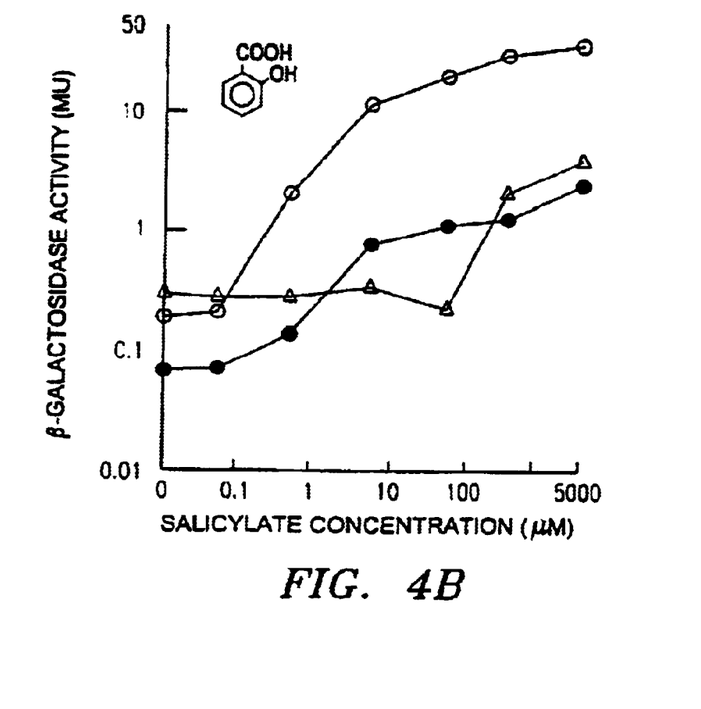

To compare the expression of lacZ from the cascade system with the simple systems that responded to salicylate, *E. coli* CC118RSL9 and CC118FH26 were used that contained insertions of the miniTn5 constructs with the nahR/Psal::lacZ and xylS2/Pm::lacZ fusions contained, respectively, in the plasmids pCNB4-lacZ and pCNB2-lacZ (de Lorenzo et al. 1993). The induction ratio in response to salicylate and the absolute values obtained by the simple systems were 10–20 times less than those obtained with the cascade system from CC1184S2PT32. Accumulation of β-galactosidase reached maximum value at 5 hours and the effective rate of synthesis was equivalent to the simple systems (FIG. 4a). At 0.5 mM of salicylate concentration the induction ratio reached 90% maximal activity. From the 10 transconjugant strains with the cascade regulatory system, the ones that produced maximal gene expression capacity (CC1184S2PT32) and maximal production of β-galactosidase (CC1184S2PT97) were selected. By SDS-PAGE and densitometry, production of β-galactosidase was estimated to be 9% of total protein in CC1184S2PT32 and about 12% in CC1184S2PT97. In contrast, less than 0.6% of β-galactosidase production was obtained with the simple system.

TABLE 1

Auxiliary plasmids for cloning into pTSPm

| Plasmid | Description | Source |
| --- | --- | --- |
| p18Not | Equivalent to pUC18 but with a EcoRI-SalI-HindIII cloning site flanked by NotI sites | (Herrero et al., 1990) |
| pUC18Not | Equivalent to pUC18 but with its MCS flanked by NotI sites | (Herrero et al., 1990) |
| pVDL8 | Low copy number plasmid derived from pSC101 replicon. It contains the same MCS that p18Not. Recommended for cloning of toxic proteins that would make impossible to maintain in high copy number plasmids such as pUC18Not | (Fernandez et al. 1996) |
| pFH2 | Origin of replication of pBR322 and M13 phage. Permits the generation in vivo of N- or C- terminal truncated proteins and provides good prokaryotic TIR for overexpression. | (Fernandez et al. 1996) |

Example 1.2

Comparison of a Cascade System in Various Configurations with a Simple System

This example illustrates the comparative use of cascade circuits for lacZ overexpression in a chromosome versus a plasmid configuration, to compare with simple circuits, and to determine relative stability.

Since the amplification of the expression could increase if the simple regulator/promoter were in a plasmid (due to the increment of gene dose), the relative convenience of using different configurations of activator/promoter to overproduce recombinant proteins was evaluated. To do this, we used the same plasmids miniTn5 but using the strain CC118λpir where they can replicate. The strains with plasmid pCNB4-lacZ or pCNB2-lacZ showed increments of 10 to 30 fold with regards to the expression in monocopy, indicating elevated gene dose. The comparison of simple (non-cacade) systems in plasmids compared to the cascade system in chromosome indicated that the basal level is 3 to 64 times less than the bacteria with pCNB4-lacZ or pCNB2-lacZ, respectively. Under induced conditions, the level of of β-galactosidase production with the cascade system in chromosome was more than two-fold of the the simple circuit nahR/Psal and 50–89% of the level of the xylS2/Pm circuit in plasmid. To combine the tight regulation with higher values of product yield, a strain with the regulatory cassette nahR/Psal::xylS2 that bears a lysogen λpir phage was constructed to allow the replication of pTSPm-lacZ. The plasmid configuration of the fusion of Pm to the heterologous gene reached the maximum level of β-galactosidase production and a lower level of basal expression with respect to the strain containing pCNB4-lacZ. However, the stability of the cascade system in the chromosomal configuration under conditions of overexpression is 100% after 40–50 generations. In contrast, the plasmid system showed bacterial populations that loses the ability to express lacZ in a extent correlating with the level of enzymatic activity in the first five hours of induction. Under induced conditions, the final concentration of viable cells in the chromosomal configuration was about 10 times more than when lacZ was overexpressed from plasmids. This observation might be explained by the presence of other genes in the plasmid necessary for replication and maintenance that are also in multicopy and whose expression may cause metabolic burden.

TABLE 2

Comparison of β-galactosidase activities and stability of the heterologous genes from the cascade and single expression systems in different configurations.

| | | [a]β-gal activity (Miller Units) | | [b]% β-gal/total proteins | | [c]lac + colonies (%) | |
| --- | --- | --- | --- | --- | --- | --- | --- |
| Strain | Plasmid | −2OHB | +2OHB | −2OHB | +2OHB | −2OHB | +2OHB |
| CC118λpir | pTSPm-lacZ | 1211 | 1358 | ND[d] | ND | 100 | 100 |
| CC118λpir | pCNB2-lacZ | 10917 | 67002 | 3.6 | 13 | 98–81 | 20–1.5 |
| CC118λpir | pCNB4-lacZ | 510 | 17952 | ND | 3.9 | 100–97 | 96–85 |
| CC4S2PMT32 | — | 171 | 30383 | ND | 8.8 | 100 | 100 |

TABLE 2-continued

Comparison of β-galactosidase activities and stability of the heterologous genes from the cascade and single expression systems in different configurations.

| Strain | Plasmid | ᵃβ-gal activity (Miller Units) | | ᵇ% β-gal/total proteins | | ᶜlac + colonies (%) | |
|---|---|---|---|---|---|---|---|
| | | −2OHB | +2OHB | −2OHB | +2OHB | −2OHB | +2OHB |
| CC4S2PMT97 | — | 408 | 39143 | ND | 11 | 100 | 100 |
| CC1184S2λpir | pTSPm-lacZ | 1487 | 78257 | ND | 20 | 100–99 | 5–0 |

Cultures were grown at 37° C. in LB with (strains with plasmids) or without ampicillin 150 μg-ml.
Dilutions 1:100 of the cultures were made in the same media without antibiotic selection and incubated for 2 hours at 37° C.
ᵃSeries of cell suspensions were incubated then with (+2OHB) or without (−2OHB) salicylate 2 mM final concentration at 30° C. β-galactosidase levels were measured enzymatically and taken for sampling SDS-PAGE after 5 hours.
ᵇMeasurements of the relative amount of β-galactosidase in cells were made by densitometry of coomasie stained 8% SDS-PAGE.
ᶜThe stability assay was accomplished by making serial batch cultures without addition of antibiotic and in the presence or absence of salicylate 2 mM at 30° C. After an estimated 40–50 generations, cultures were diluted and plated in LB agar plates with X-gal. Number of blue colonies against white colonies were counted as percentage of strains maintaining the expression system. Three independent experiments were made for each strain and conditions. As expected, deviations of stability values varied considerably among experiments with the plasmid containing strains, likely due to the stocastic appearance of the cured strains during the culture. The extreme values (max. and min.) obtained are shown. Those cases with repetitive results are shown as single values.
ᵈNot determined, = 0.5%

Example 2

Use of the Cascade System for Overexpression of a lpp'::'ompA'::'phoA Gene Within This example illustrates the use of a cascade expression system with an autoreplicative expression vector with the Pm promoter to overexpress a recombinant DNA encoding a membrane protein.

Expression of a protein from plasmid can be designed and implemented in a variety of ways and with a variety of genetic backgrounds, as the person of ordinary skill in the art is aware. The plasmids described here demonstrate but one of many possible embodiments. Specifically, the plasmids herein described above need a lysogenic λpir phage to be maintained. To avoid the requirement of the π protein for plasmid maintenance, we constructed a Pm-based expression plasmid with a autoreplicative ColE1 replication origin (derivatives) (FIG. 2b).

Plasmid pCCD5 was constructed based on pFH2 (Table I), which includes a versatile MCS that allows easy construction of truncated genes. pCCD5 contains a transcriptional terminator (rrnBTI) to reduce readthrough from promoters upstream to Pm. Since the whole expression cassette is flanked by NotI restriction sites, easy cloning into the same unique site of a variety of mini-Tn5 constructs (de Lorenzo and Timmis 1994), and subsequent introduction of the DNA constructs in strains with the CNB4-S4 minitransposon can be achieved. To test the system, we cloned a hybrid lpp'-'ompA'-'phoA sequence within. This specific fusion encodes an outer membrane protein. These are usually difficult to clone using the traditional expression systems because they damage cells when overexpressed. We used pCCD5 to pCR clone lpp'-'ompA'-'phoA from pTX101 (Francisco et al. 1991) using the oligos 5'-GAGGAATTCAATCTAGAGGGTATTAATA-3' (SEQ ID NO: 5) and 5'-CGGGATCCCCGTTGTCCGGACGAGTGCC-3' (SEQ ID NO: 6). The fragment was restricted with EcoRI and BamHI and inserted into the same sites of pCCD5, resulting in plasmid p5LOA2. A gene encoding alkaline phosphatase phoA, was cloned from pPHO7 (Gutierrez and Devedjian, 1989) as a BamHI fragment in p5LOA2 (FIG. 2b). The resultant plasmid, p5LOA2-AP, was introduced in E. coli CC1184S2 by transformation. The bacterial cultures with CC1184S2 (p5LOA2-AP) produced more than 20% of the total proteins after addition of salicylate without detection of any product in coomasie-stained SDS-PAGE in uninduced conditions. Maximal protein level was reached after 2–3 hours induction.

Example 3

Induction of a Cascade System Using Different Salicylate Derivatives

This example illustrates how the effector molecules NahR and XylS2 can synergistically amplify gene expression when integrated properly into a cascade genetic circuit. Exponential cultures of E. coli CC1184S2PMT32 (cascade) and simple circuits in E. coli strains CC118RSL9 and CC118FH26 were incubated for 5 hours at 30° C. with different benzoate derivatives (Table 3). β-galactosidase activity of the cultures incubated with the tested compounds showed that the cascade circuit has more gene expression capacity than the simple circuits (Table 3). It was observed that, in comparison to salicylate, other benzoate derivative molecules, e.g., asantranilate and 5-chloro-salicylate, could also increase β-galactosidase production by at least 10%.

TABLE 3

Induction ratio of β-galactosidase activity in the presence of different aromatic compounds

| Inducer | nahR/Psal | xylS2/Pm | nahR/Psal::xylS2/Pm |
|---|---|---|---|
| Salicylate | 24 | 13 | 235 |
| Antranilate | 22 | 11 | 285 |
| 2-Acetyl salicylate | 40 | 10 | 249 |

TABLE 3-continued

Induction ratio of β-galactosidase activity in the presence of different aromatic compounds

| Inducer | nahR/Psal | xylS2/Pm | nahR/Psal::xylS2/Pm |
|---|---|---|---|
| 4-Chloro-salicylate | 33 | 1 | 191 |
| 5-Chloro-salicylate | 32 | 3 | 268 |
| 3,5-Dichloro-salicylate | 18 | 1 | 147 |
| 5-Metoxi-salicylate | 3 | 46 | 183 |
| Benzoate | 1 | 44 | 82 |
| 3-Methyl-benzoate | 11 | 63 | 240 |
| 2-Metoxi-benzoate | 33 | 10 | 160 |
| 3-Methyl-salicylate | 17 | 46 | 218 |
| 4-Methyl-salicylate | 21 | 7 | 203 |
| 5-Methyl-salicylate | 30 | 19 | 257 |

Example 4

The Efficiency of the Amplification Cascade Depends on the Characteristics of the Terminal Positive Regulator This example illustrates that there are specific requirements for the second regulatory system to achieve the amplification of the gene expression capacity by a cascade circuit. Specifically, the activity of the target promoter should be dose-dependent over a broad range of intracellular concentrations of the second (or terminal) regulator.

Figure 5:
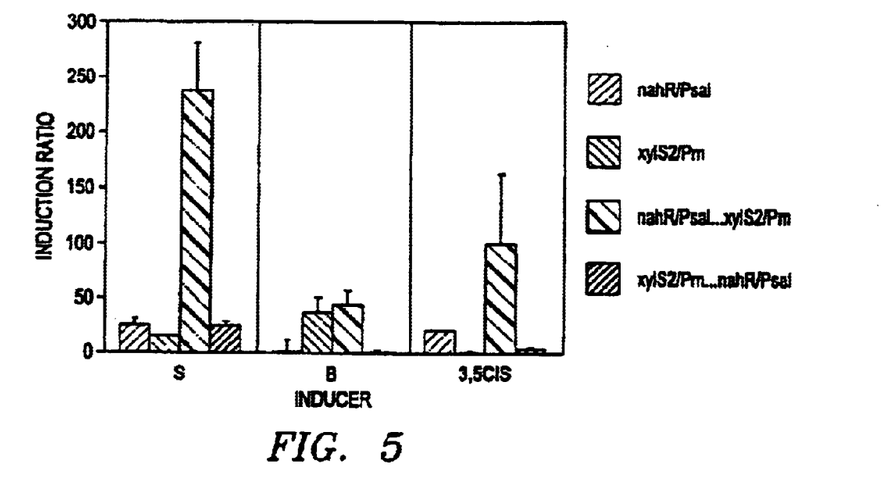
FIG. 5. Capacity for regulation of simple circuits and with two cascades using a different hierarchy of upstream and downstream regulators. S: salicylate 2 mM. B: benzoate 2 mM. 3, 5 dClS: 3, 5-dichlorosalicylate 2 mM. Basal values of β-galactosidase activity from each circuits established in E. coli were the followings: nahR/Psal (black bars), 65 MU; xylS2/Pm (open bars), 192 MU; nahR/PsalφxylS2/Pm (grey bars), 169 MU, xylS2/Pmφ tnahR/Psal (hatched bars) cascade circuit was 69 Miller Units. Data are the mean values of three independent experiments. The corresponding standard deviations are shown with the error bars.

To see the importance of the regulatory hierarchy in amplification effect, the effect of swapping the upstream and downstream regulators in the XylS2/NahR-based cascade was studied by constructing E. coli 2NRSL7. The chromosome of this strain bears the DNA elements xylS2/Pm::nahR and Psal::trp'::'lacZ carried by specialized minitransposons and was thus equivalent to E. coli strain CC1184S2PT32 except for the order of regulators in the coupled system. As shown in FIG. 5, the capacity of the reverse-coupled system responding to salicylate (24-fold induction) did not increase the capacity over the single nahR/Psal::lacZ element. Along the same line, the reversed coupled system of E. coli 2NRSL7 was completely insensitive to the XylS2-only effector benzoate. These observations indicate that overexpression of nahR does not result in a parallel increase of Psal activity, but in a non-productive excess of the second regulator because the same gene expression capacity from Psal could be achieved at a relatively low concentration of NahR. Studies on the mechanism of Psal activation indicated that the target site for this activator is occupied regardless of the induction conditions (Huang and Schell, 1991). Thus, the Psal promoter appears to depend exclusively on the presence or absence of salicylate and overexpression of nahR does not produce higher promoter activity. Taken together, these results indicate that the efficiency of the coupling in a regulatory cascade requires specific properties of the dowstream regulator/promoter which include, at least, that the activation of the final target promoter be in a dose-dependent fashion, preferably over a broad range of regulator concentrations. This is true for XylS2 but not for NahR. Thus, the mere sensitivity of the two regulators to the same effector did not grant an augmentation effect unless the appropriate hierarchy was established.

Example 5

Redesign of the Cascade System to Amplify Gene Expression in Response to Benzoate in Pseudomonas putida Example 5.1

Figure 6:
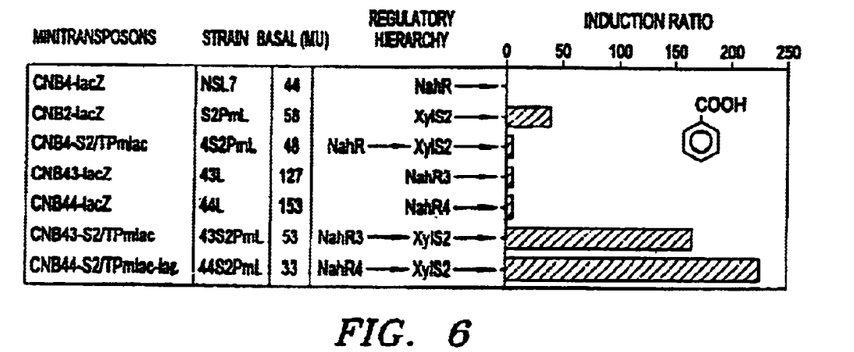
FIG. 6. Capacity for regulation of single and cascade circuits in *Pseudomonas putida*. Strains bearing in the chromosome different minitransposons (first column) containing the regulatory system described in the legend were assayed for their β-galactosidase accumulation in response to benzoate 2 mM. The fourth column displayed the regulators and sequential order in the corresponding strain. Data are mean values of three independent experiments. Basal values in Miller Units are indicated.

This example shows that the cascade amplifier system can be designed to respond to signal molecules in microorganisms other than E. coli. The design of a specialized P. putida strain bearing a benzoate cascade control circuit was performed. The rational of the circuit herein described comprises both a first regulator and a second regulator, each of which responds to benzoate. Since the downstream regulator (XylS2) already responds to this inducer (FIG. 6), the design of a new cascade involved mostly the modification of the upstream regulatory system. To this end, two nahR mutants encoding benzoate-responsive variants nahR3 and nahR4 were employed using pCNB43 and pCNB44 plasmids, respectively (Cebolla et al., 1997). They were assembled in the coupled systemse nahR3/Psal::xylS2 and nahR4Psal::xylS2, along with the reporter segment Pm::lacZ, and then inserted into the chromosome of P. putida strain KT2442 to yield P. putida 43S2PmL and P. putida 44S2PmL. The induction of these strains by benzoate was compared to that of P. putida strains bearing either the simple elements NSL7 (nahR/Psal:: lacZ), 43L (nahR3/Psal::lacZ), 44L (nahR4/Psal::lacZ) and S2PmL (xylS2/Pm::lacZ), or the cascade with the wild type benzoate-insensitive nahR variant 4S2PmL (FIG. 6). The cascade with the benzoate-responsive nahR mutants increased from 6-fold to 35-fold the gene expression capacity in response to benzoate compared to the single expression systems with nahR3, nahR4 or xylS2. In contrast, the cascade circuit with the wild type nahR in 4S2PmL (nahR/Psal:: xylS2, Pm:: lacZ) in Pseudomonas showed reduced induction capacity by benzoate (~7-fold), due to the absence of response of the upstream regulator to benzoate. These figures matched the predictions raised from the simultaneous induction of each regulator upon acquisition of the ability to respond to benzoate by NahR.

Example 5.2

This example illustrates experiments designed to eliminate the possibility that the amplification property was only a particular feature of the mutant form of XylS (XylS2) and not of the wild type.

Figure 7:
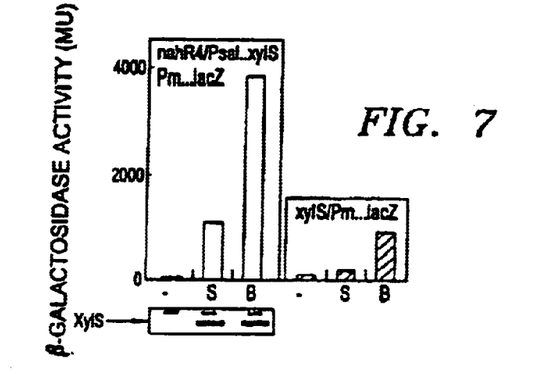
FIG. 7. Gene expression analysis of the cascade system in *P. putida* with nahR4-Psal as first regulatory system and xylS/Pm as the second one. (a) β-galactosidase accumulation without inducer (-), salicylate 2 mM (S), or benzoate 2 mM (B) with the cascade system (left) or the simple system xylS/Pm::trp'::'lacZ (right). (b) Western blot for the detection of the XylS production in cultures of *P. putida* (nahR4/Psal::xylS/Pm::trp'::'lacZ) after incubation with different effectors.

The wild type regulator xylS, able to be activated by benzoate but not by salicylate, was used as secondary regulator (Ramos et al. 1986). As a first regulator, we used an effector mutant of the nahR regulator, nahR4, that is able to recognize benzoate in addition to salicylate (Cebolla et al. 1997). To achieve this, plasmid pNS was constructed by changing the fragment NcoI from pCNB1 (de Lorenzo et al. 1993) with the corresponding one of pNS2. A NotI fragment of pNS with xylS was cloned in the corresponding NotI site of plasmid pCNB44 (Cebolla et al. 1997), resulting in plasmid pCNB44-S, that contains nahR4-Psal-:xylS, and the kanamycin resistance gene within the miniTn5 transposable sequences. The Pm::trp::lacZ fusion in pTPm-lacZ and that contained in pCNB44-S were inserted in the chromosome of Pseudomonas putida KT2442 by conjugation through the donor strain E. coli S17-1λpir, and selected with the appropriate antibiotics. Two transconjugants with the casade system were tested for their capacity to express lacZ with salicylate and benzoate. The expression level was about 4-fold higher with the cascade system than with the simple regulatory system xylS/Pm (FIG. 7). These strains also produced about 4-fold more β-galactosidase in the presence of salicylate than with benzoate. This was due to the inability of XylS to respond to salicylate as shown by western blot analysis (FIG. 7). Increased accumulation of XylS was observed when the cultures were induced with salicylate. However, XylS has weak transcriptional activity because there was no effector for XylS. In contrast to XylS accumulation in benzoate, the XylS produced is more active because of the presence of productive effector. Therefore, the presence of a common effector for both regulators is preferred for amplification effect.

References

Bentley, W. E., Morkajalili, N., Anderson, D.C., Davis, R. H. and Kompala, D. S.: Plasmid-encoded proteins: the principal factor in the "metabolic burden" associated with recombinant bacteria. Biotechnol. Bioeng. 35 (1990) 668–681.

Cebolla, A., Ruiz-Berraquero, F., and Palomares, A. J.: Stable tagging of Rhizobium meliloti with the firefly luciferase gene for environmental monitoring. Appl. Environ. Microbiol. 59 (1993) 2511–2519.

Cebolla, A., Sousa, C. and de Lorenzo, V. Effector specificity mutants of the transcriptional activator NahR of naphtalene degrading Pseudomonas define protein sites involved in binding of aromatic inducers J. Biol. Chem. 272 (1997) 3986–3992.

de Lorenzo, V., Fernádez, S., Herrero, M., Jakubzik, U. and Timmis, K. N.: Engineereing of alkyl- and haloaromatic-responsive gene expression with mini-transposons containing regulated promoters of biodegradative pathways of Pseudomonas. Gene 130 (1993b) 41–46.

de Lorenzo, V.: Designing microbial systems for gene expression in the field. Trends Biotechnol. 12 (1994) 365–371.

Dong, H., Nilsson, L. and Kurland, C. G. Gratuitous overexpression of genes in Escherichia coli leads to growth inhibition and ribosome destruction. J. Bacteriol. 177 (1995) 1497–1504.

Fellay, R., Frey, J. and Krisch, H.: Interposon mutagenesis of soil and water bacteria: a family of DNA fragment designed for in vitro insertional mutagenesis of Gram-negative bacteria. Gene 52 (1987) 147–154.

Francisco, J. A., Earhart, C. F. and Geourgiou, G.: Transport and anchoring of b-lactamase to the external surface of Escherichia coli. Proc. Natl. Acad. Sci. USA 89 (1992) 10444–10448.

Figge, J., Wright, C., Collins, C. J., Roberts, T. M., and Livingston, D. M. Stringent regulation of a stably integrated cloramphenycol acetyl transferase genes by E. coli lac repressor in monkey cells. Cell 52 (1988) 713–722

Herrero, M., de Lorenzo, V. and Timmis, K.: Transposon vectors containing non-antibiotic resistance selection markers for cloning and stable chromosomal insertion of foreing genes in gram negative bacteria. J. Bacteriol. 172 (1990) 6557–6567.

Huang, J. Z. and Schell, M. A. In vivo interactions of the NahR transcriptional activator with its target sequences. Inducer-mediated changes resulting in transcription activation J. Biol. Chem. 266 (1991) 10830–10838.

Gutierrez, C., and Devedjian, J. C. A plasmid facilitating in vivo construction of phoA gene withins in Escherichia coli. J. Bacteriol. 17 (1989) 3999.

Kahn, M., Kolter, R., Thomas, C., Figurski, D., Meyer, R., Renaut, E. and Helinski, D. R.: Plasmid cloning vehicles derived from plasmids ColE1, F, R6K, and RK2. Meth. Enzymol. 68 (1979) 268–280.

Kessler, B., Herrero, M., Timmis, K. and de Lorenzo, V. Genetic evidence that the XylS regulator of the TOL meta-operon of Pseudomonas controls Pm promoter through weak DNA-protein interaction. J. Bacteriol. 176 (1994) 3171–3176.

Laemmli, U. K.: Cleavage of structural proteins during the assembly of head of the bacteriophage T4. Nature 227 (1970) 680–685.

Makrides, S. Strategies for achieving High-level expression of genes in Escherichia coli. Microbiol. Rev. 1996, 60:512–538.

Mertens, N., Renaut, E., and Fiers, W.: Tight transcriptional control mechanism ensures stable high level expression from T7 promoter based expression plasmids. Biotechnology 13 (1995) 175–179.

Nilsson, J. and Skogman, S. G. Stabilization of Escherichia coli tryptophan-production vectors in continuous cultures:a comparison of three different systems. Biotechnology. 4 (1986) 901–903.

Ramos, J. L., Stolz, A., Reineke, W. and Timmis, K.: Altered effector specificities in regulators of gene expression: TOL plasmid xylS mutants and their use to engineer expansion of the range of aromatics degraded by bacteria. Proc. Natl. Acad. Sci. USA 83 (1986) 8467–8471.

Schein, K. H.: Production of soluble recombinant proteins in bacteria. Bio/technology 7 (1989) 1141–1149.

Suarez, A., Staendner, L. H., Rohde, M., Piatti, G., Timmis, K., and Guzman, C. Stable expression of pertussis toxin in Bordetella bronchiseptica under the control of a tightly regulated promoter. . Appl. Environ. Microbiol. 63 (1997) 122–127.

Vilette, D., Ehrlich, S. D., and Michel, B.: Transcription-induced deletions in Escherichia coli plasmids. Mol. Microbiol. 17 (1995) 493–504.

Yanisch-Perron, C., Viera, J. and J., M.: Improved M13 phage cloning vector and host strains: nucleotide sequences of the M13 mp18 and pUC19 vectors. Gene 33 (1985) 103–109.

All references cited herein are herein incorporated in their entirety. Those of skill in the art will appreciate that the spirit and scope of the invention are broad beyond the numerous embodiments already described and exemplified herein.

What is claimed is:

1. A cascade genetic circuit comprising one or more nucleic acid constructs that comprise the components:
   a) a gene encoding a Nah-R transcriptional regulator; wherein said Nah-R transcriptional regulator is responsive to one or more benzoate derivatives;
   b) a Psal promoter, wherein in the presence of at least one of said one or more benzoate derivatives, said Psal promoter is activated by said Nah-R transcriptional regulator;
   c) a gene encoding the XylS2 transcriptional regulator, wherein said gene encoding the XylS2 transcriptional regulator is regulated by said Psal promoter, and further wherein said XylS2 transcriptional regulator is responsive to at least one of said one or more benzoate derivatives; and
   d) a Pm promoter, wherein said Pm promoter is responsive to said XylS2 transcriptional regulator.

2. The cascade genetic circuit of claim 1, wherein said one or more nucleic acid constructs are provided in a prokaryotic cell.

3. The cascade genetic circuit of claim 1, wherein at least one of said one or more nucleic acid constructs is provided in a plasmid that can replicate in gram negative bacteria.

4. The cascade genetic circuit of claim 3, wherein at least one of said one or more nucleic acid constructs are provided in at least one plasmid that can promote the integration of at least one of said components of said cascade genetic circuit into the chromosome of said gram negative bacteria.

5. The cascade genetic circuit of claim 1, wherein at least one of said one or marc nucleic acid constructs is integrated into the chromosome of a gram negative bacteria.

6. The cascade genetic circuit of claim 1, wherein said one or more nucleic acid constructs are two or more nucleic acid constructs.

7. The cascade genetic circuit of claim 6, wherein said two or more nucleic acid constructs are two nucleic acid constructs.

8. The cascade genetic circuit of claim 7, wherein said two nucleic acid constructs comprise:
   a) a first nucleic acid construct that comprises a regulatory cassette comprising said gene encoding a Nah-R transcriptional regulator, said Psal promoter, and said gene encoding said XylS2 transcriptional regulator, wherein said gene encoding said XylS2 transcriptional regulator is regulated by said Psal promoter; and
   b) a second nucleic acid construct that comprises an expression cassette comprising said Pm promoter.

9. The cascade genetic circuit of claim 8, wherein said Pm promoter of said expression cassette is positioned upstream of and in proximity to one or more restriction sites, wherein the expression of a nucleic acid sequence cloned into at least one of said one or more restriction sites can be regulated by said Pm promoter.

10. A prokaryotic cell comprising the cascade genetic circuit of claim 1.

11. The prokaryotic cell of claim 10, wherein said prokaryotic cell is a gram negative bacterial cell.

12. A cascade genetic circuit comprising one or more nucleic acid constructs that comprise the components:
    a) a gene encoding a Nah-R transcriptional regulator; wherein said Nah-R transcriptional regulator is responsive to one or more benzoate derivatives;
    b) a Psal promoter, wherein in the presence of at least one of said one or more benzoate derivatives, said Psal promoter is activated by said Nah-R transcriptional regulator;
    c) a gene encoding the XylS2 transcriptional regulator, wherein said gene encoding the XylS2 transcriptional regulator is regulated by said Psal promoter, and further wherein said XylS2 transcriptional regulator is responsive to at least one of said one or more benzoate derivatives;
    d) a Pm promoter, wherein said Pm promoter is responsive to said XylS2 transcriptional regulator; and
    e) a nucleic acid sequence in proximity to said Pm promoter, wherein the expression of said nucleic acid sequence is regulated by said Pm promoter.

13. The cascade genetic circuit of claim 12, wherein said nucleic acid sequence encodes a peptide.

14. The cascade genetic circuit of claim 12, wherein said nucleic acid sequence encodes an antisense molecule, a ribozyme, an rRNA, a tRNA, an snRNA, or a diagnostic RNA molecule.

15. The cascade genetic circuit of claim 12, wherein said Nah-R transcriptional regulator is a mutant form of Nah-R selected from the group consisting of nahR3 and nahR4.

16. A prokaryotic cell comprising the cascade genetic circuit of claim 12.

17. The prokaryotic cell of claim 16, wherein said prokaryotic cell is a gram negative bacterial cell.

18. The cascade genetic circuit of claim 12, wherein at least one of said one or more nucleic acid constructs is provided in a plasmid that can replicate in gram negative bacteria.

19. The cascade genetic circuit of claim 18, wherein at least one of said one or more nucleic acid constructs are provided in at least one plasmid that can promote the integration of at least one of said components of said cascade genetic circuit into the chromosome of said gram negative bacteria.

20. The cascade genetic circuit of claim 12, wherein at least one of said one or more nucleic acid constructs is integrated into the chromosome of a gram negative bacteria.

21. The cascade genetic circuit of claim 12, wherein said one or more nucleic acid constructs are two or more nucleic acid constructs.

22. The cascade genetic circuit of claim 21, wherein said two or more nucleic acid constructs are two nucleic acid constructs.

23. The cascade genetic circuit of claim 22, wherein said two nucleic acid constructs comprise:
    a) a first nucleic acid construct that comprises a regulatory cassette comprising said gene encoding a Nah-R transcriptional regulator, said Psal promoter, and said gene encoding said XylS2 transcriptional regulator, wherein said gene encoding said XylS2 transcriptional regulator is regulated by said Psal promoter; and
    b) a second nucleic acid construct that comprises an expression cassette comprising said Pm promoter and said nucleic acid sequence in proximity to said Pm promoter.

24. A prokaryotic cell comprising the cascade genetic circuit of claim 23.

25. The prokaryotic cell of claim 24, wherein said prokaryotic cell is a gram negative bacterial cell.

26. The prokaryotic cell of claim 25, wherein said prokaryotic cell is an *E. coli* cell.

27. The prokaryotic cell of claim 25, wherein said prokaryotic cell is a *Pseudomonas putida* cell.

28. A method of inducing the expression of a nucleic acid sequence, comprising:
    a) providing or establishing the cascade genetic circuit of claim 12 in a gram negative bacteria; and
    b) contacting said grain negative bacteria with at least one benzoate derivative to induce the expression of said nucleic acid sequence.

29. The method of claim 28, wherein said nucleic acid sequence encodes a polypeptide.

30. The cascade genetic circuit of claim 12, wherein said nucleic acid sequence encodes an antisense molecule, a ribozyme, an rRNA, a tRNA, an snRNA, or a diagnostic RNA molecule.

31. The method of claim 28, wherein said benzoate derivative is salicylate or a substituted salicylate molecule.

32. The method of claim 28, wherein said gram negative bacteria is *E. coli*.

33. The method of claim 28, wherein said gram negative bacteria is *Pseudomonas putida*.

* * * * *